US010646105B2

(12) United States Patent
Li et al.

(10) Patent No.: US 10,646,105 B2
(45) Date of Patent: May 12, 2020

(54) DEVICE AND METHODS FOR COLOR CORRECTED OCT IMAGING ENDOSCOPE/CATHETER TO ACHIEVE HIGH-RESOLUTION (71) Applicant: THE JOHNS HOPKINS UNIVERSITY, Baltimore, MD (US)

(72) Inventors: Xingde Li, Ellicott City, MD (US); Anqi Zhang, Baltimore, MD (US); Jiefeng Xi, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 192 days.

(21) Appl. No.: 15/022,316

(22) PCT Filed: Sep. 17, 2014

(86) PCT No.: PCT/US2014/055988
§ 371 (c)(1),
(2) Date: Mar. 16, 2016

(87) PCT Pub. No.: WO2015/042093
PCT Pub. Date: Mar. 26, 2015

(65) Prior Publication Data
US 2016/0227990 A1  Aug. 11, 2016

Related U.S. Application Data (60) Provisional application No. 61/878,885, filed on Sep. 17, 2013, provisional application No. 61/948,826, filed on Mar. 6, 2014.

(51) Int. Cl.
A61B 5/00 (2006.01)
A61B 1/00 (2006.01)
A61B 1/002 (2006.01)

(52) U.S. Cl.
CPC .......... *A61B 1/00172* (2013.01); *A61B 1/002* (2013.01); *A61B 1/00096* (2013.01); *A61B 5/0066* (2013.01); *A61B 5/0084* (2013.01)

(58) Field of Classification Search
CPC .................................................. A61B 1/00172
See application file for complete search history.

(56) References Cited

U.S. PATENT DOCUMENTS 4,641,927 A    2/1987  Prescott
6,099,146 A *  8/2000  Imamura ................. F21V 13/04
                                                        359/558

(Continued)

OTHER PUBLICATIONS

Kuittinen et al, Encoding of efficient diffractive microlenses, 1995, Optical Society of America, vol. 20, No. 21, 2156-2158 (Year: 1995).*

(Continued)

Primary Examiner — Rochelle D Turchen
(74) Attorney, Agent, or Firm — Harrity & Harrity, LLP (57) ABSTRACT The present invention is directed to an achromatic endoscope which employs a diffractive microlens. Along with a broadband rotary joint and a custom 800 nm SD-OCT system, ultrahigh-resolution 3D volumetric imaging over a large area becomes possible. The diffractive microlens can be used directly with a GRIN lens, making the endoscope design simpler and cost effective. Preliminary ex vivo 3D intraluminal imaging was performed with the endoscope in conjunction with a home-built broadband rotary joint and a spectral-domain OCT system, demonstrating the performance of the diffractive endoscope. Considering the miniature OCT imaging probe is the required component for using the OCT technology in internal organs, the proposed approach will have a broad impact on endoscopic OCT imaging by improving OCT resolution in any applications (Continued)

that involve a miniature OCT probe, as intravascular OCT imaging, gastrointestinal (GI) tract imaging, airway imaging etc.

20 Claims, 10 Drawing Sheets (56) References Cited

U.S. PATENT DOCUMENTS

| | | | |
|---|---|---|---|
| 6,181,481 | B1 | 1/2001 | Yamamoto |
| 7,733,584 | B2 | 6/2010 | Kazakevich |
| 7,907,352 | B2 | 3/2011 | Miyano |
| 7,944,566 | B2 | 5/2011 | Xie |
| 7,952,718 | B2 * | 5/2011 | Li .................... A61B 5/0066 356/479 |
| 8,018,598 | B2 | 9/2011 | Cense |
| 2004/0254474 | A1 | 12/2004 | Seibel et al. |
| 2005/0280794 | A1 * | 12/2005 | Tsuji .................... G03F 7/70191 355/67 |
| 2009/0009771 | A1 | 1/2009 | Ostrovsky et al. |
| 2010/0157308 | A1 | 6/2010 | Xie |
| 2011/0007321 | A1 | 1/2011 | Everett et al. |
| 2011/0222020 | A1 | 9/2011 | Izatt et al. |
| 2012/0176613 | A1 * | 7/2012 | Marple .................... G02B 6/32 356/301 |

OTHER PUBLICATIONS

Zawadzki et al (2008) Ultrahigh-resolution optical coherence tomography with monochromatic and chromatic aberration correction. Opt Express. vol. 16, Iss.11: 8126-8143.

Zawadzki et al (2009) Cellular resolution volumetric in vivo retinal imaging with adaptive optics—optical coherence tomography. Opt Express. vol. 17, Iss.5: 4084-4094.

Tumlinson et al (2006) In vivo ultrahigh-resolution optical coherence tomography of mouse colon with an achromatized endoscope. J. Biomed. Opt. vol. 11, Iss.6. Online article.

Xie et al (2006) GRIN lens rod based probe for endoscopic spectral domain optical coherence tomography with fast dynamic focus tracking. Optics Express. vol. 14, Iss. 8: 3238-3246.

International Search Report and Written Opinion for Application No. PCT/US2014/055988, dated Dec. 26, 2014, 10 pages.

* cited by examiner

DEVICE AND METHODS FOR COLOR CORRECTED OCT IMAGING ENDOSCOPE/CATHETER TO ACHIEVE HIGH-RESOLUTION

CROSS-REFERENCE TO RELATED APPLICATIONS

This application is a 35 U.S.C. § 371 U.S. national entry of International Application PCT/US2014/055988, having an international filing date of Sep. 17, 2014, which claims the benefit of U.S. Provisional Application No. 61/878,885, filed Sep. 17, 2013, U.S. Provisional Application No. 61/948,826, filed Mar. 6, 2014, the content of each of the aforementioned applications is herein incorporated by reference in their entirety.

GOVERNMENT SUPPORT

This invention was made with government support under grant no. EB010021 and CA183430 awarded by the National Institutes of Health. The government has certain rights in the invention.

FIELD OF THE INVENTION

The present invention relates generally to medical imaging. More particularly, the present invention relates to a device and method for color corrected OCT imaging.

BACKGROUND OF THE INVENTION

OCT is a noninvasive, high-resolution optical imaging technology capable of real-time imaging of tissue microanatomy with a few millimeter imaging depth and can be envisioned as an optical analog of ultrasound B-mode imaging, except that it utilizes near infrared light rather sound waves. Compared to ultrasound, OCT does not require a matching gel and the resolution of OCT can be 50-100 times finer than ultrasound. OCT can thus function as a form of "optical biopsy", capable of assessing tissue microanatomy and function with a resolution approaching that of standard histology but without the need for tissue removal. The axial resolution of OCT is governed by the spectral bandwidth of the light source and it is inversely proportional to the source spectrum bandwidth. Chromatic aberration in the OCT imaging optics will alter the backreflected spectrum from the target, resulting in the loss of OCT axial resolution. The change in the backreflected spectrum from the sample could also result in the increase in the side lobes of the OCT imaging signal, which again will lead to the loss of OCT axial resolution. In addition, as in conventional imaging optics, the chromatic aberration will focus light of different colors to different spots, thus degrading the OCT lateral resolution as well. In a benchtop imaging system such as a microscope, chromatic aberration in the imaging optics is routinely corrected by using achromatic lenses (e.g. lenses made of multi elements with different refractive index profiles and surface curvatures). But, such approaches are not cost effective or practical to be implemented in miniature OCT imaging probes.

Miniature endoscopes are a critical component in the OCT technology, enabling translational applications for imaging internal luminal organs such as the gastrointestinal tract or airways. Most OCT endoscopes developed so far were designed for imaging at 1300 nm, which provides 2-3 mm imaging depth and 8-30 µm axial resolution. However, there is an increasing need to develop an ultrahigh-resolution OCT endoscope for resolving fine structures (e.g. under 5 µm) such as airway smooth muscle or structural changes associated with early stage diseases. Benefiting from the availability of broadband light sources at 800 nm, ultrahigh-resolution OCT imaging has been demonstrated at such wavelength with bench-top systems. For the endoscopic setting, due to the challenges such as management of chromatic aberration over a broadband spectral bandwidth, there are only few achromatic endoscopic setups. The designs in those endoscopes are rather complicated and expensive, involving multi-element achromatic microlenses.

Accordingly, there is a need in the art for a miniature OCT device and a cost-effective and practically implemented method for color corrected OCT imaging.

SUMMARY OF THE INVENTION

The foregoing needs are met, to a great extent, by the present invention which provides a device for obtaining OCT images from a subject including a miniature OCT imaging probe configured to obtain high-resolution images of the subject and a diffraction element configured to mitigate wavelength dependent aberration in the high-resolution images obtained by the OCT imaging probe.

In accordance with an aspect of the present invention, the diffraction element includes a diffractive lens. The diffractive lens is positioned at a distal end of a compound lens within the OCT imaging probe. The diffractive lens can have a high diffraction efficiency over a broad spectral range, such as approximately 800 to approximately 1050 nm. The wavelength dependent aberration takes the form of a chromatic aberration.

In accordance with another aspect of the present invention a method for mitigating achromatic aberration in OCT imaging includes using a diffraction element integrated into miniature imaging optics of an OCT imaging probe, wherein the OCT imaging probe comprises a broadband lightsource. The method also includes reducing a longitudinal focal shift of the broadband light source, such that different colors of light in the broadband light source will be focused to a small spot for achieving high lateral resolution. Additionally, the method includes minimizing distortion to a backreflected spectral at a given imaging depth, such that OCT axial resolution is improved to an optimal axial resolution afforded by the broadband lightsource.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to an achromatic endoscope which employs a diffractive microlens. Along with a broadband rotary joint and a custom 800 nm SD-OCT system, ultrahigh-resolution 3D volumetric imaging over a large area becomes possible. The diffractive microlens can be used directly with a GRIN lens, making the endoscope design simpler and cost effective. Preliminary ex vivo 3D intraluminal imaging was performed with the endoscope in conjunction with a home-built broadband rotary joint and a spectral-domain OCT system, demonstrating the performance of the diffractive endoscope. Considering the miniature OCT imaging probe is the required component for using the OCT technology in internal organs, the proposed approach will have a broad impact on endoscopic OCT imaging by improving OCT resolution in any applications that involve a miniature OCT probe, such as intravascular OCT imaging, gastrointestinal (GI) tract imaging, airway imaging etc.

Figure 1A:
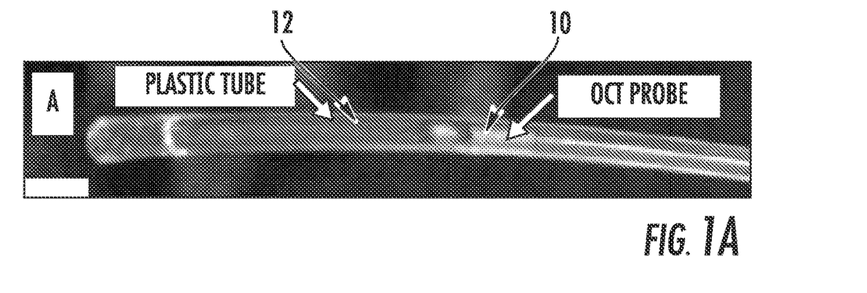
FIG. 1A illustrates a photo of a representation of a miniature OCT imaging probe/endoscope for internal luminal imaging.
Figure 1B:
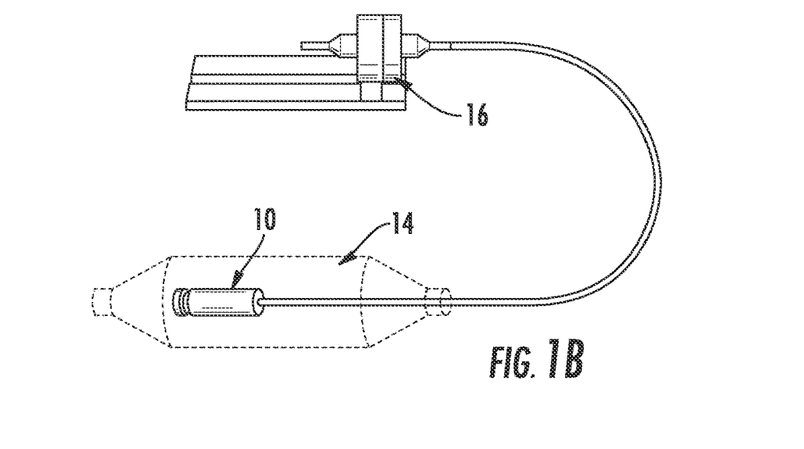
FIG. 1B illustrates a photo image of an OCT imaging probe situated within a transparent plastic balloon for imaging of large lumens.
Figure 1C:
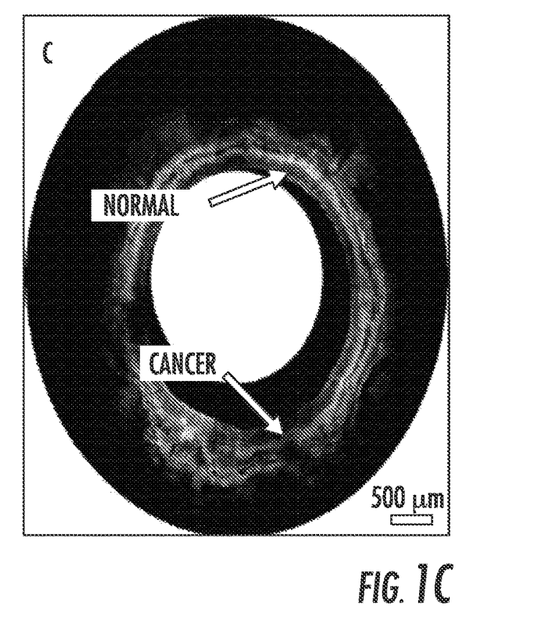
FIG. 1C illustrates a representative OCT image of a human esophagus showing the difference between normal and cancerous tissue.

Miniature OCT imaging probes are an essential component for many translational applications of OCT such as intravascular imaging for high risk plaque detection, intra esophageal or GI tract imaging for cancer detection and many others. FIGS. 1A-1C illustrate exemplary OCT probes and an exemplary resultant image. Particularly FIG. 1A illustrates a photo of a representation of a miniature OCT imaging probe/endoscope 10 for internal luminal organ imaging. The probe was encased in a transparent plastic tube 12. FIG. 1B illustrates an OCT imaging probe 10 situated within a transparent plastic balloon 14 for imaging of large lumens (such as the GI tract). The device illustrated in FIG. 1B can also include a rotary joint 16 for 3D imaging. FIG. 1C illustrates a representative OCT image of a human esophagus showing that the normal (layered structure) and cancerous (nodules) regions can be discerned.

Figure 2:
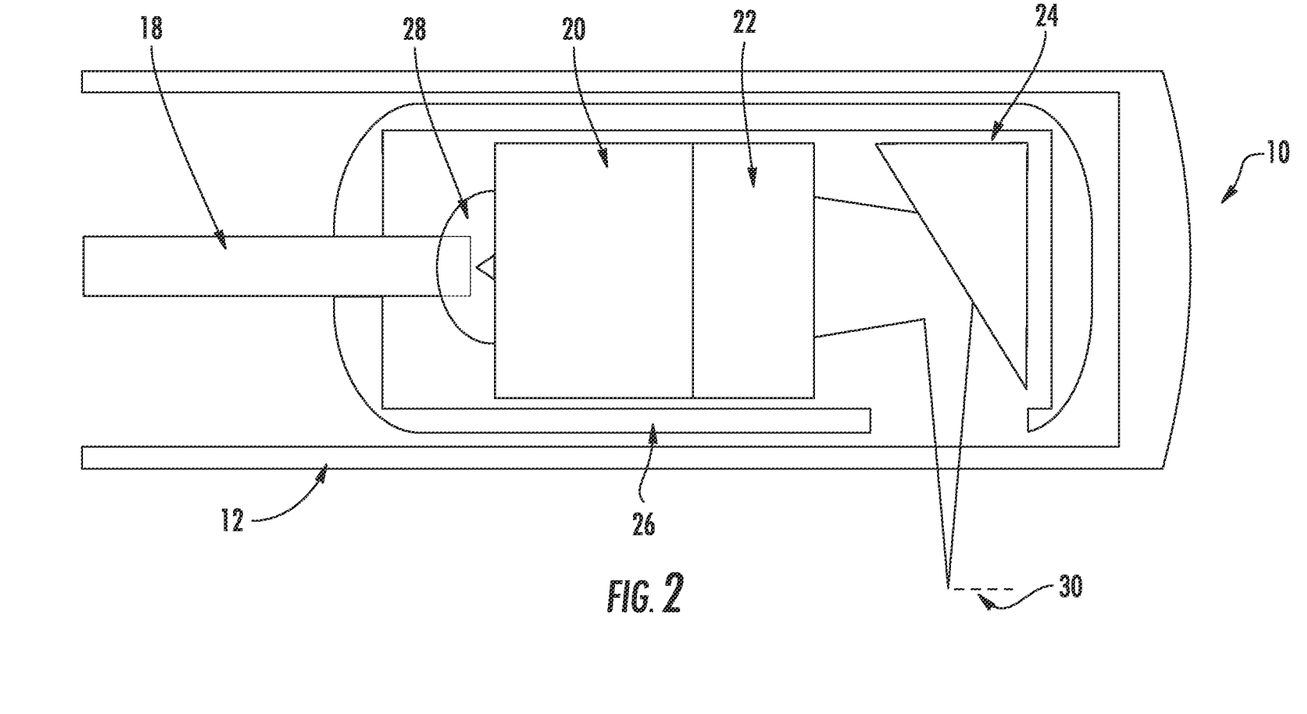
FIG. 2 illustrates a schematic diagram of a distal end of a miniature OCT probe.

FIG. 2 illustrates a schematic diagram of a distal end optics design for a miniature OCT imaging probe 10, which entails (not limited to) a single-mode optical fiber (SMF) 18, a glass rod spacer 20, a miniature beam focusing lens 22, a micro beam reflector 24, a protective guard 26, and a transparent plastic sheath 12. In miniature OCT imaging probes, a GRIN lens is often used for beam focusing which is cost effective and easy to implement. However, a GRIN lens comes with chromatic aberration, compromising both the axial and lateral resolution. Correction of chromatic aberration in such miniature imaging probes becomes very challenging due to the probe size (diameter and rigid length) restriction. Although the concept of using a multi-element lens similar to a microscope objective can be introduced to the miniature OCT imaging probes for correcting the chromatic aberration (as we demonstrated before), this approach would be very challenging and impractical due to prohibitive cost and increased probe size. Optical glue 28 can be used to couple the SMF 18 to the spacer 20. FIG. 2 also illustrates the point of the beam focus 30 after the beam is reflected off of micro-reflector 24.

The present invention provides a solution to overcome the long-existing problem of chromatic aberration in miniature OCT probes by introducing a diffractive element/mask to the imaging lens. The diffractive element will diffract light of different wavelengths to slightly different directions, which effectively changes the beam path for each wavelength. With a proper design, the path changes induced by the diffractive element/mask can be opposite to the changes caused by chromatic aberration, thus compensating the chromatic aberration.

Figure 3:
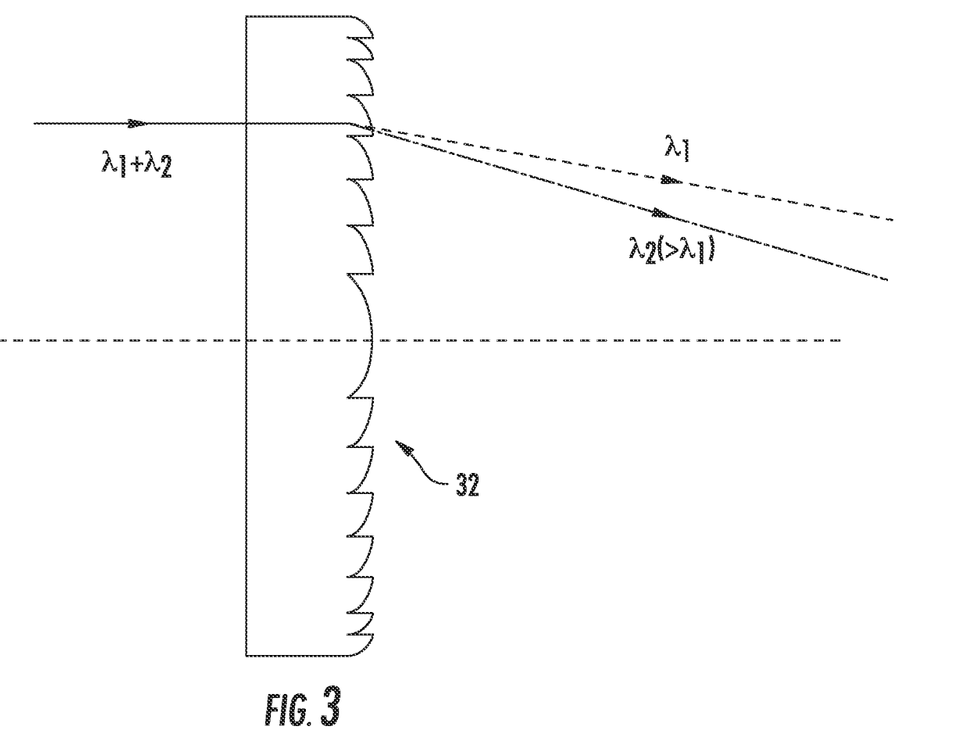
FIG. 3 illustrates a schematic diagram of a representative pattern of a diffractive element or mask, according to an embodiment of the present invention.

FIG. 3 illustrates a representative schematic of such a diffractive element/mask for use with an OCT probe according to the present invention. In this design, the longer wavelength can be bent more towards the optical axis, which is opposite from the chromatic aberration effect. The diffractive element/mask 32 can be made very small in size and very large in quantity (through mass microfabrication), and it can be easily introduced to the imaging optics of an OCT probe at its distal end, e.g. by sandwiching between some optics or attached to the end of the GRIN lens. As illustrated in FIG. 3 a longer wavelength ($\lambda_2$) will be bent more towards the optical axis than shorter wavelength ($\lambda_1$), which is opposite from what occurs in chromatic aberration. Thus, the combination of such a diffractive element with a focus lens can mitigate chromatic aberration.

Figure 4A:
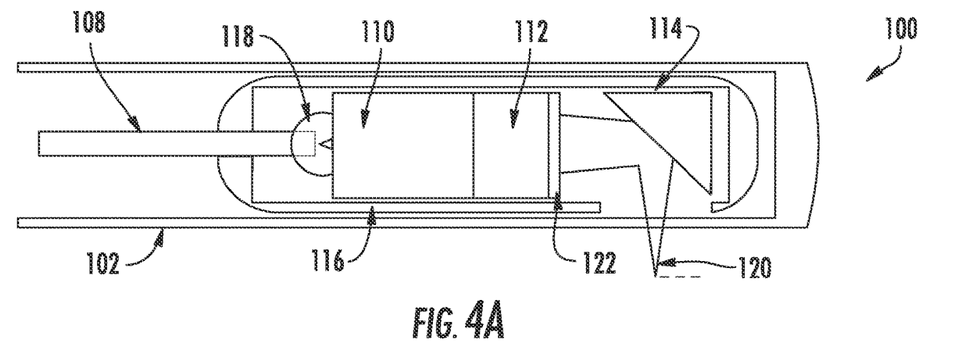
FIGS. 4A-4C illustrate representative schematic diagrams of a distal end of an imaging probe with a built in diffractive element, according to an embodiment of the present invention.
Figure 4B:
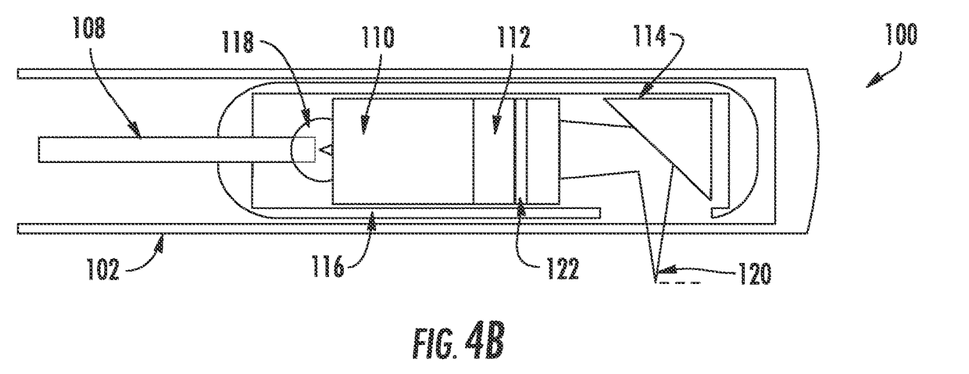
Figure 4C:
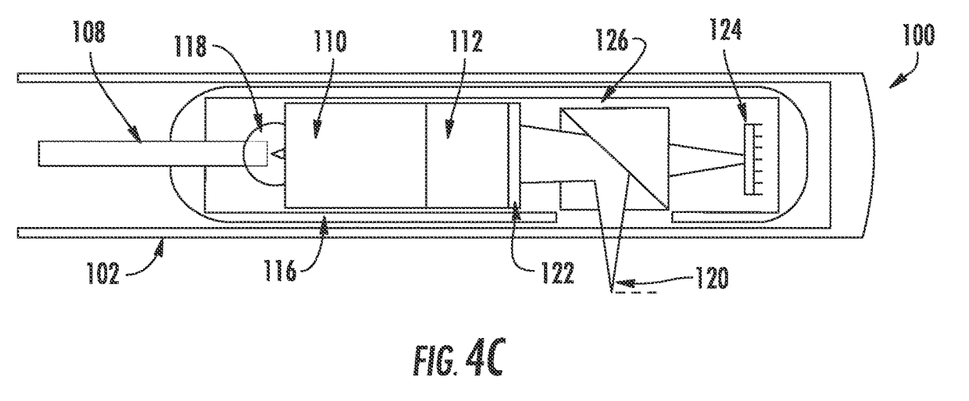

FIGS. 4A-4C illustrate schematic diagrams of several configurations for a miniature imaging probe with a diffractive element according to an embodiment of the present invention. As illustrated in FIGS. 4A, 4B, and 4C, the OCT device 100 includes an SMF 108 coupled to spacer 110 with optical glue 118. A GRIN lens 112 is disposed at a proximal end of the spacer 110. A micro reflector 114 is positioned proximally of the GRIN lens 112 and directs the beam toward beam focus 120. The OCT device 100 is disposed within a plastic tube 102 and also includes protective guard 116. Each of FIGS. 4A, 4B, and 4C also include a diffractive element 122 incorporated into the design. As illustrated in FIG. 4A, the diffractive element 122 is attached to the end of the GRIN lens 112. As illustrated in FIG. 4B, the diffractive element 122 is sandwiched between two pieces of the GRIN lens 112 where the beam is nearly parallel to the optical axis, and as illustrated in FIG. 4C, a micro beam splitter 126 and a mirror 124 are built in at the distal end to form a common path diffractive imaging probe.

Figure 5:
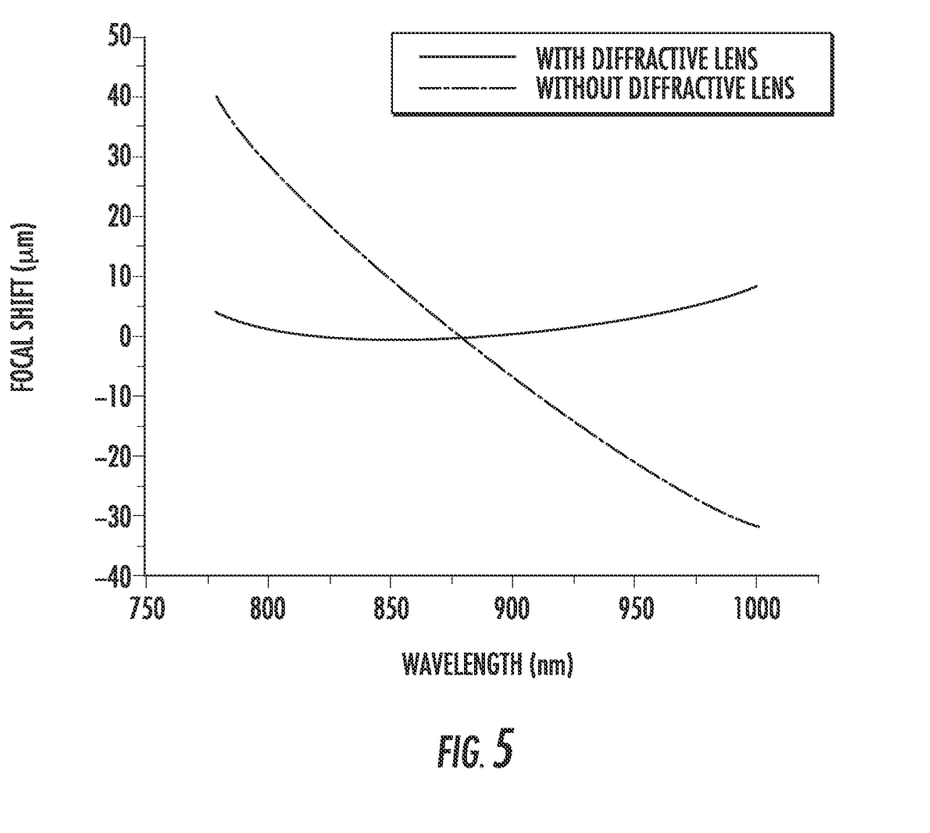
FIG. 5 illustrates a graphical representation of a longitudinal focal shift for a conventional GRIN lens for a conventional (dashed line) and a diffractive (solid line) imaging probe.

Simulations have been performed to investigate the performance of the proposed approach. As shown in FIG. 5, the chromatic aberration of a typical GRIN lens based miniature OCT imaging probe, represented by the longitudinal focal shift, is about 100 um. When a properly designed diffractive element is added to the distal end optics of the miniature imaging probe, the chromatic aberration is dramatically reduced, resulting in a much smaller longitudinal focal shift down to 10 um. FIG. 5 illustrates a graphical view of a longitudinal focal shift for a conventional GRIN lens based OCT imaging probe (dashed line) and for a diffractive OCT imaging probe which has a built-in diffractive element (solid line) over the wavelength range of 780-1020 nm. Longitudinal focal shift represents the severity of chromatic aberration in an imaging probe. It is noticed that the longitudinal focal shift is reduced by almost 10 times (i.e. from about 100 µm down to about 10 µm) when using a diffractive element, showing the effective correction of chromatic correction by the diffractive element.

The proposed approach is demonstrated by implementing an off-the-shelf diffractive element to a miniature OCT imaging probe. It is noted that the diffractive element in the proof-of-the-concept experiments was not optimized for the specific broadband OCT light source with a spectral bandwidth from 780 nm to 1020 nm. Instead it only covered a portion (880-1120 nm) of our OCT source spectrum. To demonstrate the feasibility of the proposed concept, the spectra backreflected from a mirror placed at the focal plane of the imaging probe was measured and also measured at other parallel planes with a given distance away from the focal plane. In an ideal case (i.e. for an imaging probe without any chromatic aberration), the backreflected spectra should not change much with the mirror position.

Figure 6:
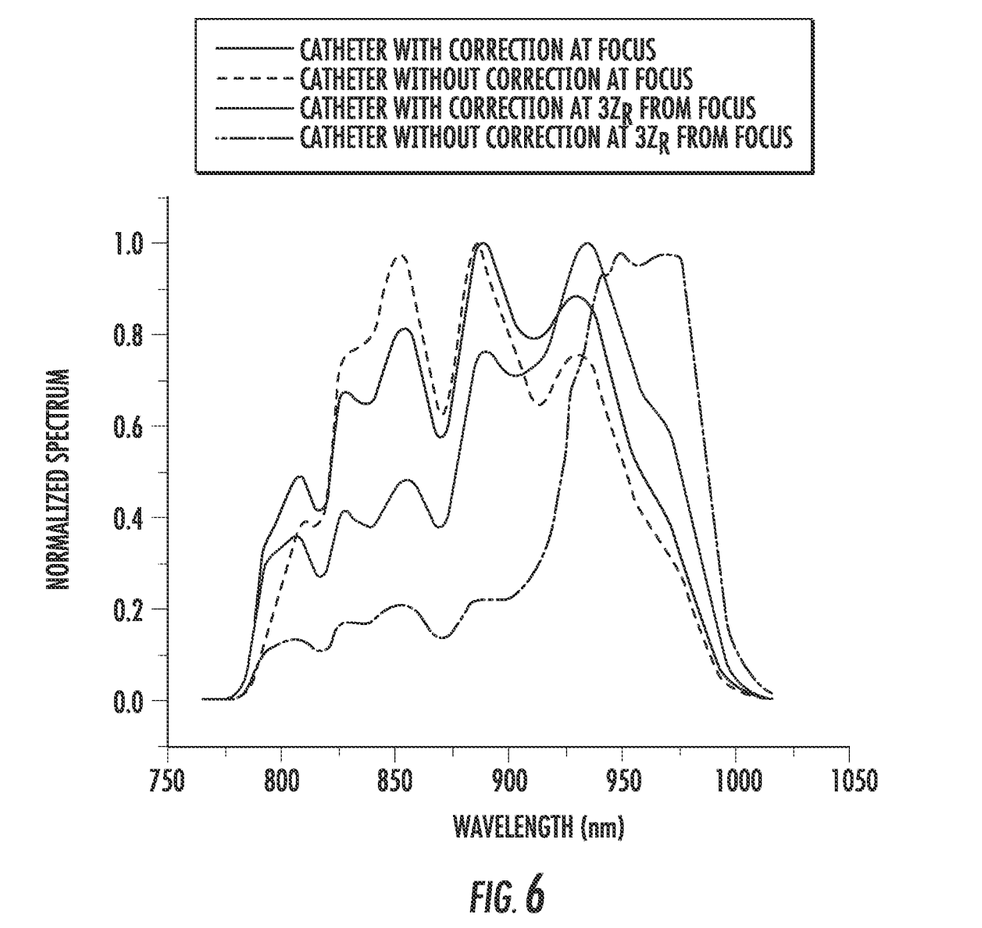
FIG. 6 illustrates a graphical view of a spectra backreflected by a mirror placed at a focal plane and a plane 3 Rayleigh lengths ($3Z_R$) away from the focal plane for a conventional GRIN lens-based OCT imaging probe catheter and for a diffractive OCT imaging catheter.

FIG. 6 illustrates a graphical view of the spectra backreflected from a mirror placed at the focal plane and a parallel plane 3ZR away from the focal plane (i.e. 3 times of the Rayleigh length which is about 1.5 times of the standard depth of view). The spectra experienced some changes when the mirror was moved away from the focal plane, particularly at the shorter wavelength side. This change is expected since the diffractive element was not specifically designed to accommodate the whole spectrum of the OCT light source and it was only supposed to cover the wavelengths longer than 880 nm. For comparison, the backreflected spectra were also collected by a conventional OCT imaging probe with the same design as the diffractive probe except that this conventional probe does not have the diffractive element. Clearly the backreflected spectrum was severely modified when the mirror was moved away from the focal plane, suggesting the basic concept that the proposed diffractive imaging probe works in correcting/mitigating chromatic aberration. With a specifically designed diffractive element according suitable for the OCT source spectrum, more improvement on chromatic aberration in a miniature imaging probe will be achieved.

Figure 7A:
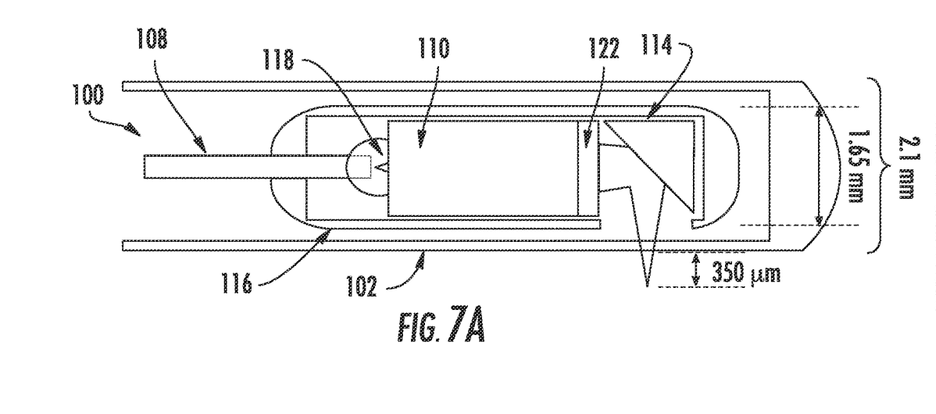
FIG. 7A illustrates a schematic diagram of an OCT endoscope according to an embodiment of the present invention.
Figure 7B:
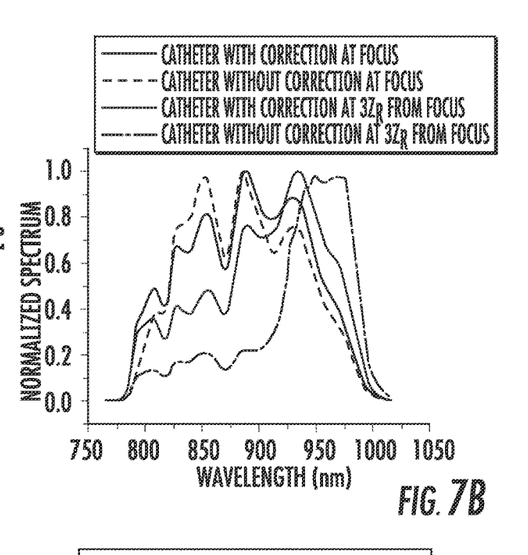
FIG. 7B illustrates a spectra backreflected by a mirror placed at a focal plane and a plane 3 Rayleigh lengths ($3Z_R$) away from the focal plane for a conventional GRIN lens-based OCT imaging probe catheter and for a diffractive OCT imaging catheter.
Figure 7C:
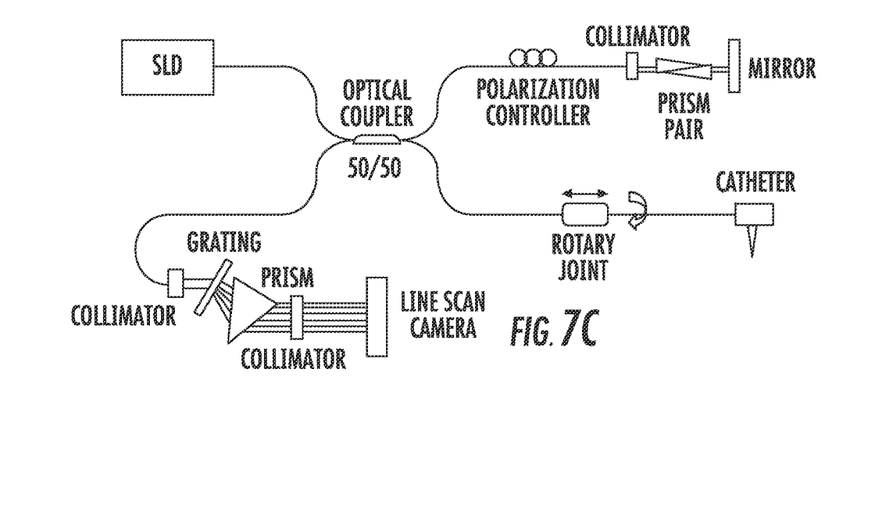
FIG. 7C illustrates a schematic diagram of a configuration of an 800 nm broadband endoscopic SC-OCT system.
Figure 7D:
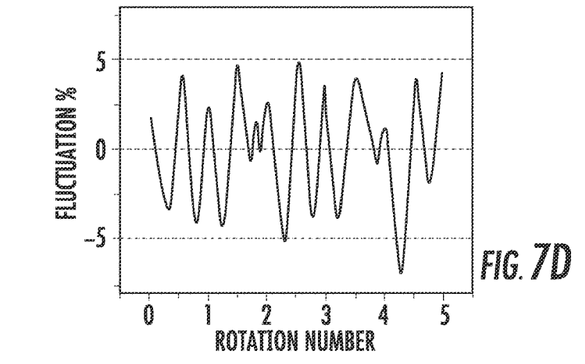
FIG. 7D illustrates a graphical view of fluctuation of a rotary joint coupling efficiency at 5 fps.

FIG. 7A illustrates a schematic diagram of an endoscope according to an embodiment of the present invention. In this OCT device 100 A 125 µm single-mode fiber 108 at 800 nm is glued onto a compound lens 110 which is made of a glass rod and a GRIN rod lens with a 1 mm diameter. To manage the chromatic aberration, a custom-made diffractive lens 122 with high diffraction efficiency over a broad spectral range (800-1050 nm) but very weak focusing power is placed behind the compound lens 110. A 45° reflector 114 is attached to the end of the endoscope to bend the beam 90° for circumferential imaging. Another endoscope with the same design as the above one but without the diffractive lens was also built for comparison. To show the effect of the diffractive lens on compensating chromatic aberration, the spectrum reflected by a mirror at the focal point of the endoscope is compared with that reflected at three Rayleigh lengths (i.e. 3ZR) away from the focal point for both endoscopes, as illustrated in FIG. 7B. The results clearly indicate much reduced chromatic aberration in the endoscope with the aid of diffractive lens. The SD-OCT endoscopic imaging system is illustrated in FIG. 7C, where a broadband super luminescence diode (SLD) from Superlum Ltd. with a full spectral bandwidth of ~240 nm centering at 870 nm is employed as the light source. The light source is delivered into the sample and reference arms through a broadband 50/50 fiber coupler. In the sample arm, a home-made broadband fiber rotary joint is used to connect the stationary fiber and the endoscope that is to be rotated. The rotary joint is mounted on a translational stage to enable 3D volumetric imaging. The fluctuation of light coupling efficiency of the rotary joint was controlled as low as 12% as shown in FIG. 7D. In order to match the dispersion in two arms, a prism pair was inserted into reference arm to minimize the air gap in the reference arm. The residual dispersion mismatch between the two arms was numerically compensated. For detection, a custom-designed, home-built linear-in-wavenumber spectrometer is employed. The line scan camera has 2048 pixels and a maximum line scan rate of 70 k/second at 12 bit resolution. Real-time OCT imaging is rendered by a custom C++ program, which controls the system synchronization, real-time data acquisition, signal processing, data storage, etc. The endoscope with the diffractive lens is measured to have a 3.75 µm axial resolution in air and 6.15 µm lateral resolution.

Figure 8A:
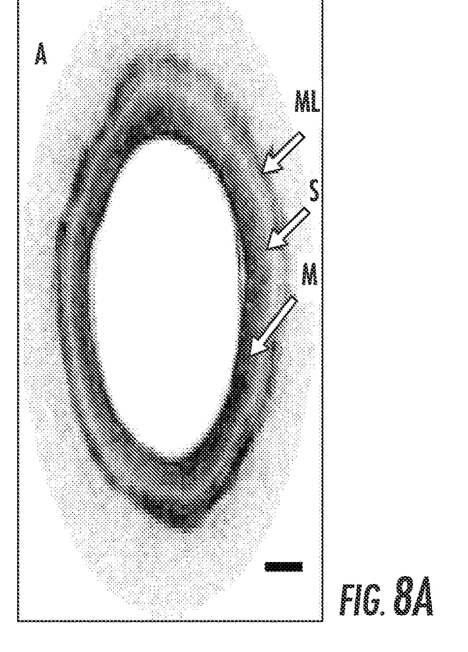
FIGS. 8A-8D illustrate ex vivo real time images of a guinea pig esophagus and a rat trachea.
Figure 8B:
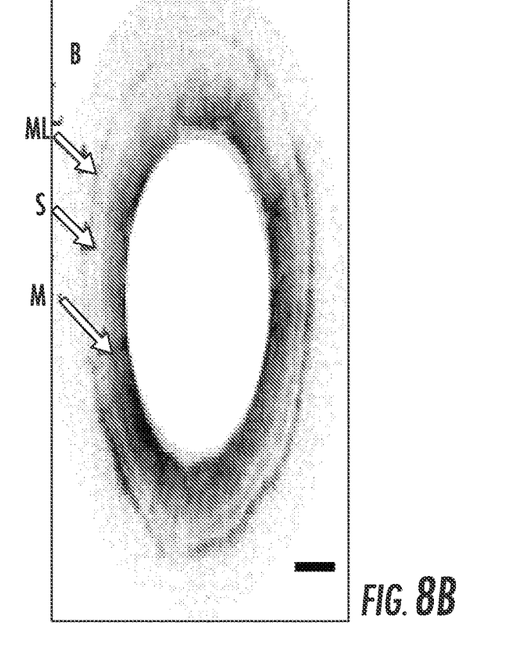
Figure 8C:
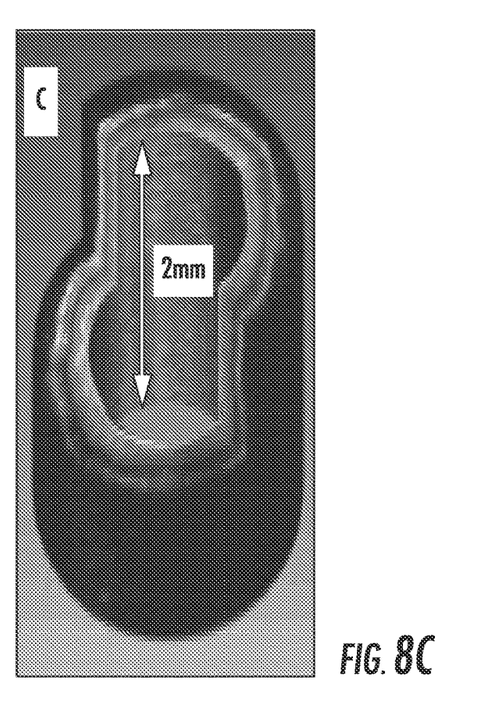
Figure 8D:
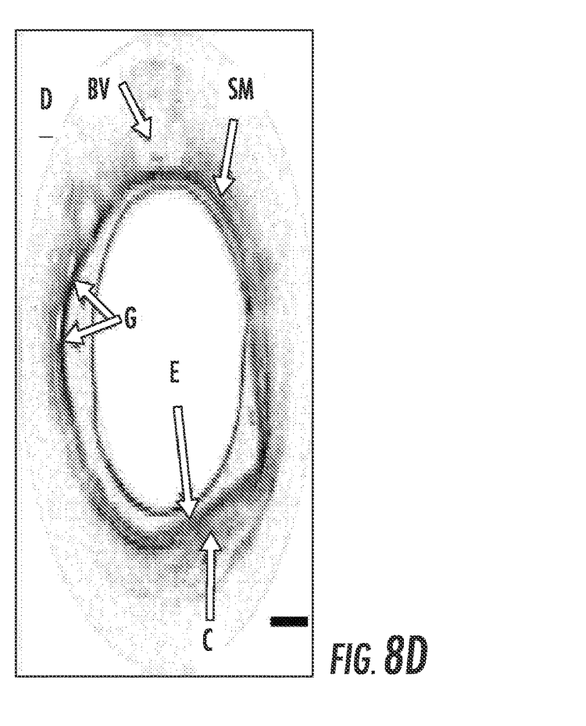

Real time ex vivo imaging study of guinea pig esophagus was performed using the diffractive endoscope along with the SD-OCT system. For comparison, the same tissue was also imaged with an endoscope without a diffractive lens. FIGS. 8A and 8B illustrate representative cross-sectional esophageal images acquired by the endoscope with and without a diffractive lens, respectively. The OCT system was running at 5 frames per second (fps) and each frame consisted of 2048 A-scans. Layer structures such as mucosa, submucosa and muscular layer can be identified on FIG. 8A, while some parts of the muscular layer become difficult to resolve on FIG. 8B. It is clear that the quality of the OCT image acquired with the endoscope without a diffractive lens experienced dramatic degradation. The imaging results indicate that the reduced chromatic aberration by using a diffractive lens is able to significantly improve the OCT image quality. FIG. 8C shows a representative 3D volumetric image of the esophagus acquired by the diffractive endoscope by pulling back the rotating endoscope with a 10 μm pitch. In addition to esophagus, ex vivo rat trachea was also imaged using the diffractive endoscope running at 10 fps. One representative cross-sectional image is shown in FIG. 8D. Some fine structures such as epithelium, cartilage, glands and smooth muscle can be observed.

Figure 9A:
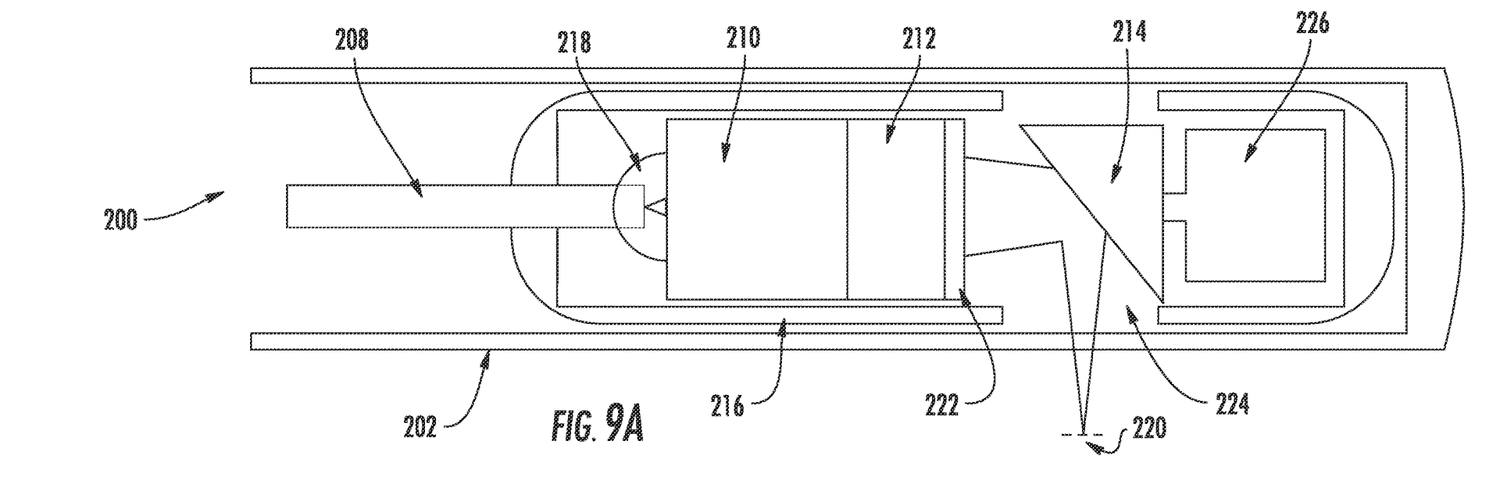
FIGS. 9A and 9B illustrate schematic diagrams of the imaging probe at its distal end with a built in diffractive element and a micromotor, according to an embodiment of the present invention.
Figure 9B:
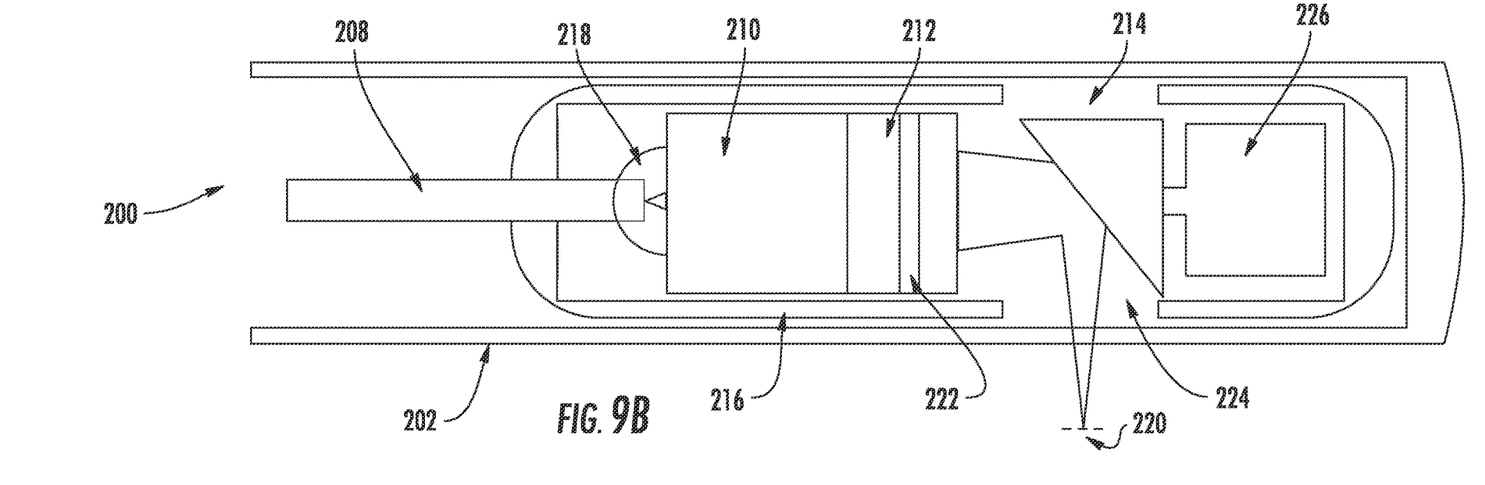

FIGS. 9A and 9B illustrate schematic diagrams of the imaging probe at its distal end with a built in diffractive element and a micromotor, according to an embodiment of the present invention. As illustrated in FIGS. 9A and 9B, the OCT device 200 includes an SMF 208 coupled to spacer 210 with optical glue 218. A lens 212 is disposed at a proximal end of the spacer 210. A micro reflector 214 is positioned proximally of the lens 212 and directs the beam toward beam focus 220. The OCT device 200 is disposed within a plastic tube 202 and also includes protective guard 216. Each of FIGS. 9A and 9B also include a diffractive element 222 incorporated into the design. More particularly, FIG. 9A illustrates that the diffractive element 222 is attached to the end of a microlens 212. With respect to FIG. 9B, the diffractive element 222 is sandwiched between the two microlenses 212, such that the beam is nearly parallel to the optical axis. Circumferential imaging is performed by rotating a beam reflector or microprism. FIG. 9A also illustrates a micromotor 226 to rotate the reflector incorporated into the OCT device 200 and also a cut-opening or transparent window 224.

Figure 10A:
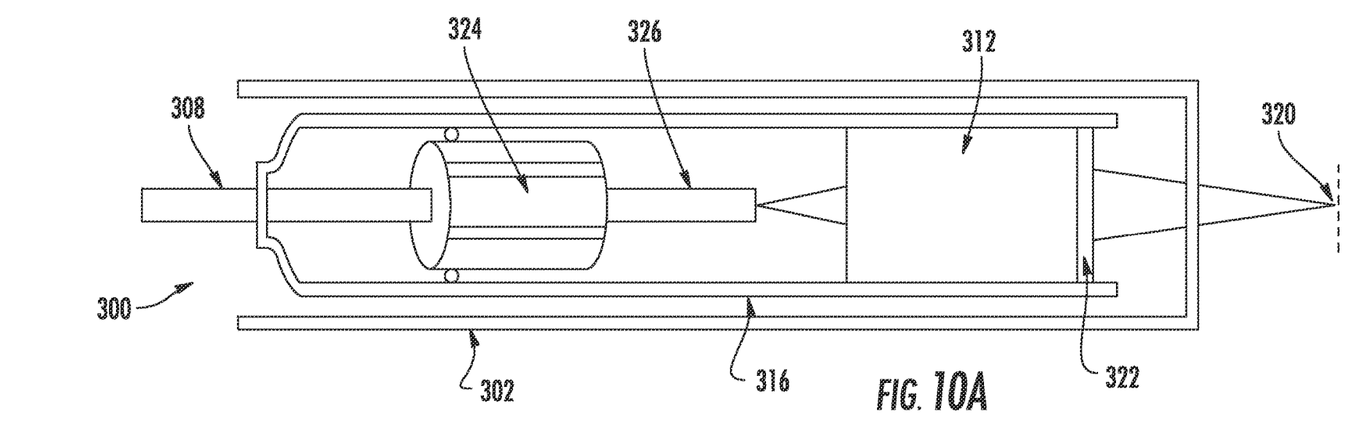
FIGS. 10A and 10B illustrate schematic diagrams of the imaging probe at its distal end with a built-in diffractive element and a beam scanner, according to an embodiment of the present invention.
Figure 10B:
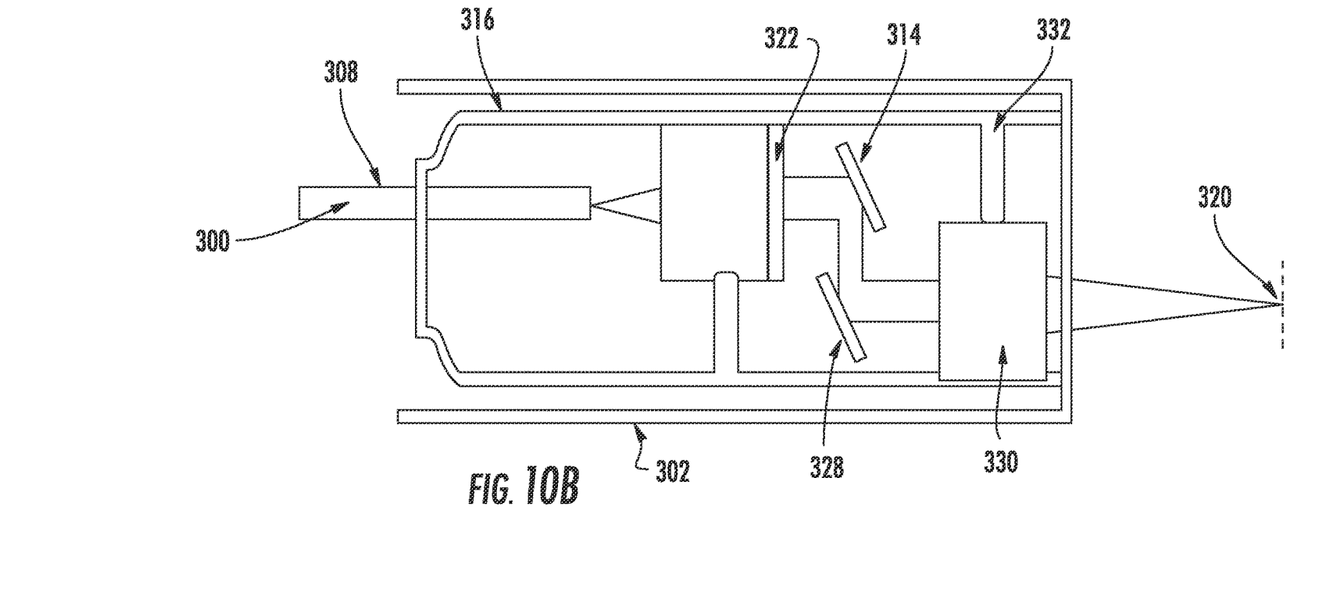

FIGS. 10A and 10B illustrate schematic diagrams of the imaging probe at its distal end with a built-in diffractive element and a beam scanner, according to an embodiment of the present invention. As illustrated in FIGS. 10A and 10B, the OCT device 300 includes an SMF 308 coupled to spacer 310 with optical glue 318. A lens 312 is disposed at a proximal end of the spacer 310. A micro reflector 314 is positioned proximally of the lens 312 and directs the beam toward beam focus 320. The OCT device 300 is disposed within a plastic tube 302 and also includes protective guard 316. Each of FIGS. 10A and 10B also include a diffractive element 322 incorporated into the design. More particularly, FIG. 10A illustrates a PZT actuated fiber scanner 324 and FIG. 10B illustrates a MEMS beam scanner 328. Beam scanning is performed at the distal end of the probe by using a micromotor to rotate a reflector (for achieving circumferential imaging), or a fiber scanner 324 or an MEMS scanner 328 to scan the beam (where forward-viewing imaging is possible). Thus the entire endoscope does not have to rate for achieving beam scanning. This avoids the use of a fiber-optic rotary joint, which could be the bottleneck for sped or spectral bandwidth, in addition to all the potential artifacts associated with fiber endoscope rotation. As illustrated in FIG. 10A a SMF cantilever 326 is included in the device. As illustrated in FIG. 10B, the device includes a second lens 330 to focus the beam after processing by the MEMS scanner 328. A lens support 332 can also be included.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A device for obtaining optical coherence tomography (OCT) images from a subject, comprising:
   a miniature OCT imaging probe configured to obtain high-resolution images of the subject;
   wherein the miniature OCT imaging probe comprises:
      a housing including a protective guard;
      an optical fiber, positioned within the housing and the protective guard,
         a portion of the optical fiber extending from the protective guard;
      a microlens, positioned within the protective guard, and having a 1 mm diameter or less;
      a microreflector positioned within the protective guard, the microreflector being positioned adjacent to the microlens, and
         the microreflector being configured to direct a beam;
      a micromotor configured to rotate the microreflector; and
   a microfabricated diffraction element for mitigating chromatic aberrations coupled to the microlens and being configured to mitigate wavelength dependent aberration in the high-resolution images obtained by the miniature OCT imaging probe,
      the microfabricated diffraction element being pre-fabricated with a pattern of diffraction portions so that beam paths associated with different wavelengths are changed so as to be opposite to changes caused by chromatic aberration to thereby focus the changed beam paths onto a spot for achieving high axial and lateral resolution,
      the microfabricated diffraction element having a high diffraction efficiency,
      the microfabricated diffraction element reducing a longitudinal focal shift of the miniature OCT imaging probe to as low as 10 μm,
      the microfabricated diffraction element being sized to fit within a miniature endoscope for focusing the miniature endoscope, and
      the protective guard including a cut-opening to direct the beam upon reflection.

2. The device of claim 1 wherein the microfabricated diffraction element comprises a diffractive lens.

3. The device of claim 2 wherein the diffractive lens is positioned at a distal end of a compound lens within the OCT imaging probe.

4. The device of claim 2 wherein the diffractive lens comprises a predetermined diffraction efficiency over a broad spectral range.

5. The device of claim 4 wherein the broad spectral range is between 800 to 1050 nm.

6. The device of claim 1 wherein the wavelength dependent aberration comprises a chromatic aberration.

7. A method for mitigating achromatic aberration in optical coherence tomography (OCT) imaging, comprising:
   providing a microfabricated diffraction element coupled to a lens of a miniature OCT imaging probe having a 1 mm diameter or less,
   wherein the miniature OCT imaging probe comprises a broadband light source,
      the microfabricated diffraction element being pre-fabricated with a pattern of diffraction portions so that beam paths associated with different wavelengths are changed so as to be opposite to changes caused by chromatic aberration to thereby focus the changed beam paths onto a spot for achieving high axial and lateral resolution, the microfabricated diffraction element having a high diffraction efficiency, the microfabricated diffraction element reducing a longitudinal focal shift of the miniature OCT imaging probe to as low as 10 μm, and the microfabricated diffraction element being sized to fit within a miniature endoscope for focusing the miniature endoscope, and reducing the longitudinal focal shift of the miniature OCT imaging probe, such that different colors of light in the broadband light source are focused to the spot for achieving high axial and lateral resolution; and minimizing distortion to a back reflected spectral at a given imaging depth, such that OCT axial resolution is improved to an optimal axial resolution afforded by the broadband light source.

8. A device for obtaining optical coherence tomography (OCT) images from a subject, comprising:
a miniature OCT imaging probe configured to obtain high-resolution images of the subject;
wherein the miniature OCT imaging probe comprises:
a housing including a protective guard;
a microlens, positioned within the protective guard, having a 1 mm diameter or less;
a piezoelectric (PZT) actuated fiber scanner,
the PZT actuated fiber scanner including an optical fiber,
the optical fiber being positioned within the housing and the protective guard, and
a portion of the optical fiber extending from the protective guard; and
a microfabricated diffraction element coupled to the microlens,
the microfabricated diffraction element being configured to mitigate wavelength dependent aberration in the high-resolution images obtained by the miniature OCT imaging probe,
the microfabricated diffraction element being prefabricated with a pattern of diffraction portions so that beam paths associated with different wavelengths are changed so as to be opposite to changes caused by chromatic aberration to thereby focus the changed beam paths onto a spot for achieving high axial and lateral resolution,
the microfabricated diffraction element having a high diffraction efficiency,
the microfabricated diffraction element reducing a longitudinal focal shift of the miniature OCT imaging probe to as low as 10 μm, and
the microfabricated diffraction element being sized to fit within a miniature endoscope for focusing the miniature endoscope.

9. The device of claim 8 wherein the microfabricated diffraction element comprises a diffractive lens.

10. The device of claim 9 wherein the diffractive lens is positioned at a distal end of a compound lens within the OCT imaging probe.

11. The device of claim 9 wherein the diffractive lens comprises a predetermined diffraction efficiency over a broad spectral range.

12. The device of claim 11 wherein the broad spectral range is between 800 to 1050 nm.

13. The device of claim 8 wherein the wavelength dependent aberration comprises a chromatic aberration.

14. A device for obtaining optical coherence tomography (OCT) images from a subject, comprising:
a miniature OCT imaging probe configured to obtain high-resolution images of the subject;
wherein the miniature OCT imaging probe comprises:
a housing including a protective guard;
an optical fiber, positioned within the housing and the protective guard,
a portion of the optical fiber extending from the protective guard;
a first microlens, positioned within the protective guard, having a 1 mm diameter or less;
a microelectromechanical systems (MEMS) beam scanner, positioned within the protective guard, configured to scan a beam;
a microreflector,
the microreflector being positioned adjacent to the first microlens, and
the microreflector being configured to direct the beam toward the MEMS beam scanner;
a second lens, positioned with the protective guard, configured to focus the beam after processing by the MEMS beam scanner; and,
a microfabricated diffraction element coupled to the first microlens,
the microfabricated diffraction element being configured to mitigate wavelength dependent aberration in the high-resolution images obtained by the miniature OCT imaging probe,
the microfabricated diffraction element being prefabricated with a pattern of diffraction portions so that beam paths associated with different wavelengths are changed so as to be opposite to changes caused by chromatic aberration to thereby focus the changed beam paths onto a spot for achieving high axial and lateral resolution,
the microfabricated diffraction element having a high diffraction efficiency,
the microfabricated diffraction element reducing a longitudinal focal shift of the miniature OCT imaging probe to as low as 10 μm, and
the microfabricated diffraction element being sized to fit within miniature endoscope for focusing the miniature endoscope.

15. The device of claim 14 wherein the microfabricated diffraction element comprises a diffractive lens.

16. The device of claim 15 wherein the diffractive lens is positioned at a distal end of a compound lens within the OCT imaging probe.

17. The device of claim 15 wherein the diffractive lens comprises a predetermined diffraction efficiency over a broad spectral range.

18. The device of claim 17 wherein the broad spectral range is between 800 to 1050 nm.

19. The device of claim 14 wherein the wavelength dependent aberration comprises a chromatic aberration.

20. The device of claim 1, further comprising:
a glass spacer positioned between the optical fiber and the microlens,
the glass spacer being secured to the optical fiber via optical glue.

* * * * *